(12) United States Patent
Iannotti et al.

(10) Patent No.: US 9,011,452 B2
(45) Date of Patent: Apr. 21, 2015

(54) POSITIONING APPARATUS AND METHOD FOR A PROSTHETIC IMPLANT (71) Applicant: The Cleveland Clinic Foundation, Cleveland, OH (US)

(72) Inventors: Joseph P. Iannotti, Strongsville, OH (US); Wael K. Barsoum, Bay Village, OH (US); Jason A. Bryan, Avon Lake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/340,868

(22) Filed: Jul. 25, 2014

(65) Prior Publication Data

US 2014/0336657 A1 Nov. 13, 2014

Related U.S. Application Data (62) Division of application No. 13/226,948, filed on Sep. 7, 2011, now Pat. No. 8,821,499.

(51) Int. Cl.
A61F 2/46 (2006.01)
A61B 17/17 (2006.01)
A61B 17/15 (2006.01)
A61B 17/56 (2006.01)
A61B 19/00 (2006.01)
A61F 2/30 (2006.01)

(52) U.S. Cl.
CPC .............. A61F 2/4603 (2013.01); A61B 17/15 (2013.01); A61B 2017/568 (2013.01); A61B 2019/507 (2013.01); A61B 2019/508 (2013.01); A61F 2/4607 (2013.01); A61F 2002/30542 (2013.01); A61F 2002/4687 (2013.01); A61B 17/17 (2013.01)

(58) Field of Classification Search
CPC .................................. A61B 17/17; A61F 2/46
USPC ............................................. 606/86 R, 87–89
See application file for complete search history.

(56) References Cited

U.S. PATENT DOCUMENTS 5,768,134 A 6/1998 Swaelens et al.
6,206,884 B1 3/2001 Masini (Continued)

FOREIGN PATENT DOCUMENTS

JP 11244315 9/1999
WO 2009001083 12/2008

Primary Examiner — Christopher Beccia
(74) Attorney, Agent, or Firm — Norton Rose Fulbright Canada LLP (57) ABSTRACT A positioning apparatus for guiding resection of a patient tissue and guiding placement of a prosthetic implant component in a desired implant position with respect to the resected patient tissue and method of use are described. A locating block includes a mating surface contoured for mating contact with the patient tissue. A cutting plane indicator provides a physical indication of a desired cutting plane for the resection. A placement indicator is spaced apart from the locating block and includes a component-contacting feature. An elongate spacing arm is operative to space the placement indicator apart from the locating block. The spacing arm is configured to place the component-contacting feature of the placement indicator at a predetermined placement position in three-dimensional space relative to the patient tissue. The placement position predetermination is at least partially based upon pre-operative imaging of the patient tissue.

10 Claims, 6 Drawing Sheets

(56) References Cited

U.S. PATENT DOCUMENTS

| | | |
|---|---|---|
| 7,601,155 B2 | 10/2009 | Petersen |
| 2003/0176860 A1 | 9/2003 | Shimura |
| 2005/0148843 A1 | 7/2005 | Roose |
| 2008/0234685 A1 | 9/2008 | Gjerde |
| 2009/0087276 A1 | 4/2009 | Rose |
| 2009/0222015 A1 | 9/2009 | Park et al. |
| 2009/0222016 A1 | 9/2009 | Park et al. |
| 2009/0254093 A1 | 10/2009 | White et al. |

POSITIONING APPARATUS AND METHOD FOR A PROSTHETIC IMPLANT

RELATED APPLICATIONS

This application is a divisional of U.S. patent application Ser. No. 13/226,948 filed Sep. 7, 2011 which claims priority from U.S. Provisional Application No. 61/380,476, filed Sep. 7, 2010, the subject matter of both of which is incorporated herein by reference.

TECHNICAL FIELD

The present invention relates to a positioning apparatus and method for a prosthetic implant and, more particularly, to a method and apparatus for guiding resection of a patient tissue and guiding placement of a prosthetic implant component in a desired implant position with respect to the resected patient tissue.

BACKGROUND OF THE INVENTION

Minimally invasive surgery ("MIS") is quickly becoming standard for the implantation of prosthetic components into a patient. For example, the use of an MIS hip replacement technique involves a skin incision of approximately 7 cm and is performed without the previously required laying-open of the patients entire hip area. MIS techniques for joint replacement may reduce trauma to the patient, with less pain, less blood loss, shorter convalescence, faster stabilization, and fewer post-operative restrictions on exercising of the joint. The use of MIS may also give the prosthetic joint a better fixation and function than traditional surgery, which in turn can contribute to an increased lifetime for the prosthetic joint. MIS also can be done with considerably shorter hospitalization time than traditional techniques, and may even be available for outpatient procedures, providing an economic benefit linked to positive patient outcome in many cases.

Prosthetic hip joint replacement, whether accomplished via MIS or any other suitable surgical technique, is performed by the head of the femur being cut off and replaced by a femoral component that is fixed down in the femoral canal. A ball is mounted on the femoral component and mates with a cup that is fixed in the pelvis, or vice versa. One factor which may lead to success for a total hip replacement technique is the provision of a clear overall view of the wound during the operation in order to achieve precise surgery and the desired positioning for the prosthetic components. In the precise surgery associated with the implantation of a hip replacement prosthetic component, it is important for the head of the femur to be removed with great precision. For this purpose an osteotomy template generally used, whereby the level and orientation of the planned cutting plane is transferred to the patient's femur to guide the surgeon. With the pre-operative planning procedures that are currently under development, a computer model of the patient's femur will often be produced, based on CT, radiographic, or other pre-operatively obtained images. Based on this model (including various considerations, e.g., height, version, and/or offset), a desired cutting plane for the patient's femur can be determined.

In a shoulder environment, the humeral head is removed and replaced with a prosthetic head which is fixed to the bone using a stem within the humeral metaphysis or diaphysis shaft. The humeral head articulates with the native glenoid (hemiarthroplasty) or with a prosthetic glenoid component. The humeral osteotomy is made at or near the anatomic neck of the humerus. This osteotomy defines a humeral head neck shaft angle and version of the final implant. In patients with deformity associated with arthritis, the anatomic neck may be difficult to define, making it difficult for the surgeon to determine to precise location of this osteotomy. Standard generic stock cutting guides currently used for this procedure still require the surgeon to identify these anatomic landmarks to place the cutting guides.

Osteotomy templates exist for use in conventional surgery, but there is currently a need for improved osteotomy templates. A resection guide for use in many hip, shoulder, or other types of prosthetic replacements, whether using MIS or another surgical style, would be useful than currently used guides by being considerably smaller, intended for insertion through different openings, employing different anatomical landmarks, allowing for a more accurate osteotomy, and easier to position in the planned position than the currently used resection guides.

Since traditional osteotomy templates are not adapted to the individual patient, they require the patients to have relatively similar anatomical characteristics. This means that for patients with anatomical deviations, there is a reduction in precision with traditional multi-use osteotomy templates, thereby giving a final result that is not optimal. For patients with greater anatomical deviations, moreover, the majority of multi-use templates will be difficult to use on account of limitations in the possibilities for adjustment. Even for patients without great deviations, when using multi-use templates it will be necessary to carry out adjustments of the osteotomy template during the operation, resulting in an increased risk of error, increased operating time and thereby an increased risk of complications.

SUMMARY OF THE INVENTION

In an embodiment of the present invention, a positioning apparatus for guiding resection of a patient tissue and guiding placement of a prosthetic implant component in a desired implant position with respect to the resected patient tissue is described. A locating block includes a mating surface contoured for mating contact with the patient tissue. The mating surface is custom-configured for the patient tissue responsive to pre-operative imaging of the patient tissue. A cutting plane indicator provides a physical indication of a desired cutting plane for the resection. The cutting plane indicator is positioned on the locating block to guide a cutting implement in performing the resection of the patient tissue along the desired cutting plane when the mating surface is in mating contact with the patient tissue. A placement indicator is spaced apart from the locating block and includes a component-contacting feature. An elongate spacing arm is operative to space the placement indicator apart from the locating block. The spacing arm has oppositely disposed first and second spacing arm ends. The first spacing arm end is attached to the locating block and the second spacing arm is attached to the placement indicator. The spacing arm is configured to place the component-contacting feature of the placement indicator at a predetermined placement position in three-dimensional space relative to the patient tissue. The placement position predetermination is at least partially based upon pre-operative imaging of the patient tissue. When the prosthetic implant component is being placed with respect to the resected patient tissue, a preselected surface of the prosthetic implant component is brought into contact with the component-contacting feature to indicate that the prosthetic implant component has achieved the desired implant position.

In an embodiment of the present invention, a method of guiding resection of a patient tissue and guiding placement of a prosthetic implant component in a desired implant position with respect to the resected patient tissue is described. A mating surface of a locating block is placed in mating contact with the patient tissue. The mating surface is custom-configured for the patient tissue responsive to pre-operative imaging of the patient tissue to allow a single locating block mating orientation relative to the patient tissue. A physical indication of a desired cutting plane for the resection is provided using a cutting plane indicator included on the locating block. A placement indicator, spaced apart from the locating block and including a component-contacting feature, is provided. The placement indicator is spaced apart from the locating block with an elongate spacing arm. The spacing arm has oppositely disposed first and second spacing arm ends. The first spacing arm end is attached to the locating block and the second spacing arm is attached to the placement indicator. The component-contacting feature of the placement indicator is placed at a predetermined placement position in three-dimensional space relative to the patient tissue with the spacing arm. The placement position predetermination is at least partially based upon pre-operative imaging of the patient tissue. A cutting implement is guided with the cutting plane indicator to resect the patient tissue along the desired cutting plane when the mating surface is in mating contact with the patient tissue. The prosthetic implant component is placed in an initial implant position with respect to the patient tissue. The prosthetic implant component is adjusted with respect to the patient tissue to bring the prosthetic implant component toward a desired implant position. A preselected surface of the prosthetic implant component is brought into contact with the component-contacting feature to indicate that the prosthetic implant component has achieved the desired implant position.

In an embodiment of the present invention, a system for guiding resection of a femoral head and guiding placement of a prosthetic hip implant component in a desired implant position with respect to the resected femoral shaft is described. A locating block includes a mating surface contoured for mating contact with the femoral shaft. The mating surface is custom-configured for the femoral shaft responsive to pre-operative imaging of the femoral shaft. A cutting plane indicator provides a physical indication of a desired cutting plane for the resection. The cutting plane indicator is positioned on the locating block to guide a cutting implement in performing the resection of the femoral head along the desired cutting plane when the mating surface is in mating contact with the femoral shaft. A placement indicator includes a component-contacting feature. An elongate spacing arm is operative to space the placement indicator apart from the locating block. The spacing arm has oppositely disposed first and second spacing arm ends. The first spacing arm end is attachable to the locating block and the second spacing arm is attached to the placement indicator. The spacing arm, when attached to the locating block, is configured to place the component-contacting feature of the placement indicator at a predetermined placement position in three-dimensional space relative to the femoral shaft. The placement position predetermination is at least partially based upon pre-operative imaging of the femoral shaft. The locating block includes a spacing arm coupling feature for selectively receiving the first spacing arm end. When the prosthetic hip implant component is being placed with respect to the resected femoral head, a preselected surface of the prosthetic hip implant component is brought into contact with the component-contacting feature to indicate that the prosthetic hip implant component has achieved the desired implant position.

BRIEF DESCRIPTION OF THE DRAWINGS

For a better understanding of the invention, reference may be made to the accompanying drawings, in which.

DESCRIPTION OF EMBODIMENTS

Figure 1:
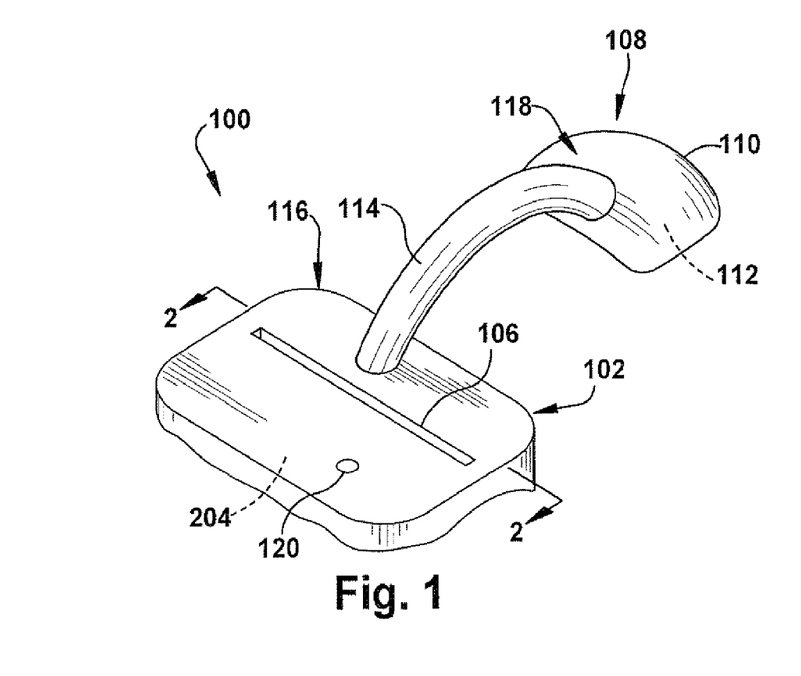
FIG. 1 is a schematic top view of an embodiment of the present invention.

In accordance with the present invention, FIG. 1 depicts a schematic view of a positioning apparatus 100 for guiding resection of a patient tissue (not shown) and guiding placement of a prosthetic implant component (not shown) in a desired implant position with respect to the resected patient tissue. The patient tissue is shown and described herein as a femur and the prosthetic implant component is shown and described herein as a femoral prosthetic hip component, but the patient tissue and corresponding prosthetic implant component could be any desired types such as, but not limited to, hip joints, shoulder joints, knee joints, ankle joints, phalangeal joints, metatarsal joints, spinal structures, long bones (e.g., fracture sites), or any other suitable use environment for the present invention.

The positioning apparatus 100 includes a locating block 102. The locating block 102 includes a mating surface (204, shown in cross-section in FIG. 2), the mating surface being custom-configured for the patient tissue responsive to pre-operative imaging of the patient tissue. For example, the mating surface 204 could be at least partially configured through the use of computer tomography ("CT") data of the patient tissue. Additionally or alternatively, the mating surface 204 could be at least partially configured through use of patient scans including digital or analog radiography, magnetic resonance imaging, or any other suitable imaging means. The patient tissue pre-operative images are optionally displayed for review and manipulation before/during configuration of the mating surface 204, such as through the use of a computer or other graphical workstation interface. The configuration of the mating surface 204 is described herein as being performed using three-dimensional images; however, one or more two-dimensional depictions of the patient tissue may also or instead be consulted during configuration of the mating surface 204.

Figure 2:
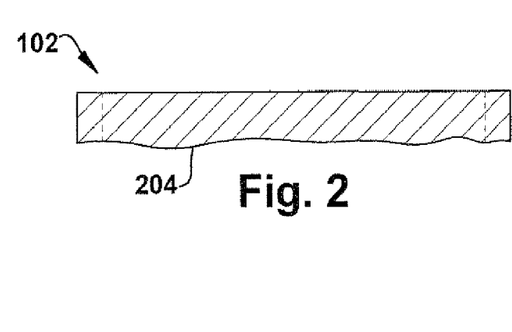
FIG. 2 is a cross-sectional view taken along line 2-2 of FIG. 1.

The mating surface 204 is configured to mate with a surface of the patient tissue, as will be discussed below. The term "mate" is used herein to indicate a relationship in which the contours of two structures are at least partially matched or coordinated in at least two dimensions. In the described mating relationship, the mating surface 204 mates or nests into contact with the surface of the patient tissue to provide the locating block 102 with at least one of location and stabilization assistance with respect to the patient tissue.

The locating block 102 also includes a cutting plane indicator 106 providing a physical indication of a desired cutting plane for the resection. The cutting plane indicator 106 is positioned on the locating block 102 to guide a cutting implement (not shown) in performing the resection of the patient tissue along the desired cutting plane when the mating surface 204 is in mating contact with the patient tissue. The cutting plane indicator 106 could be a (closed) cutting slot, as shown in the Figures, an (open) cutting plateau forming an edge of the locating block 102, or may have any other suitable form for providing a physical indication of a desired cutting plane for the resection.

Optionally, the cutting plane indicator 106 may be positioned on the locating block 102 for guiding contact with the cutting implement performing the resection of the patient tissue. In other words, the cutting plane indicator 106 may be configured to directly support and guide the cutting implement (either a cutting edge/structure or a non-cutting/support surface) via direct contact, which may be sliding or otherwise relatively moving contact between the cutting plane indicator and the cutting implement. An alternate way for the cutting plane indicator 106 to guide the cutting implement might be for the user to keep the cutting implement a predetermined distance from the cutting plane indicator without allowing direct contact therebetween.

A placement indicator 108 is spaced apart from the locating block 102 and includes a component-contacting feature 110. The component-contacting feature 110 may be a component-contacting surface 112 shaped to mate with a preselected surface (not shown) of the prosthetic implant component (as will be described below) to indicate that the prosthetic implant component has achieved a desired implant position. For example, if the preselected surface of the prosthetic implant component is concave or convex, the component-contacting surface 112 may at least partially mirror that concavity or convexity. The component-contacting surface 112 could be as small or large as desired for a particular application of the present invention. For example, the component-contacting surface 112 could contact the preselected surface of the prosthetic implant component using a contact area of any size range between a single-point contact and an entire-preselected-surface-area contact.

The positioning apparatus 100 also may include an elongate spacing arm 114 operative to space the placement indicator 108 apart from the locating block 102. The spacing arm 114 has oppositely disposed first and second spacing arm ends 116 and 118, respectively. The first spacing arm end 116 is attached, permanently or temporarily, to the locating block 102 and the second spacing arm end 118 is attached, permanently or temporarily, to the placement indicator 108. The spacing arm 114 is configured to place the component-contacting feature 110 of the placement indicator 108 at a predetermined placement position in three-dimensional space relative to the patient tissue. The placement position predetermination may be at least partially based upon preoperative imaging of the patient tissue.

Optionally, the spacing arm 114 may be separately provided from the locating block 102. In such instance, the locating block 102 may include a spacing arm coupling feature (not shown) for selectively receiving the first spacing arm end 118. For example, the spacing arm coupling feature could be a notch, socket, aperture, pin, pincers, or any other suitable structure positioned on the locating block 102 and configured to selectively receive and hold the first spacing arm end 118, possibly in conjunction with a complementary feature (not shown) of the spacing arm 114. It may be desirable to provide at least one of the spacing arm 114 and the spacing arm coupling feature with an orienting structure to limit the relative orientation(s) in which the spacing arm can be coupled to the locating block 102.

The locating block 102 may include a locating pin aperture 120 configured for engagement with a locating pin (not shown), separately associated with the patient tissue. When present, the locating pin, in cooperation with the locating pin aperture 120, may assist with providing at least one of securement, stability, and position indication for the locating block relative to at least one of the patient tissue and a prosthetic implant component.

Figure 3:
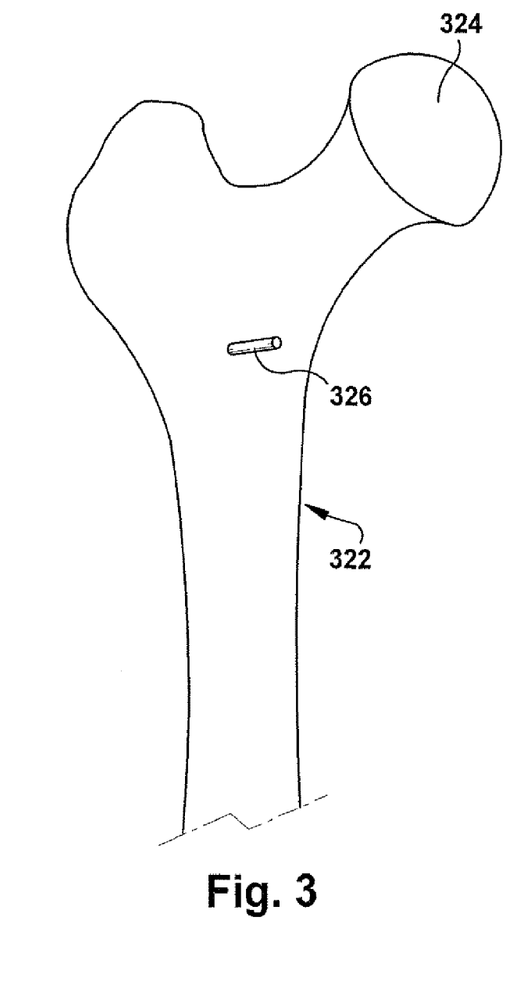
FIGS. 3-9 schematically depict a sequence of operation of the embodiment of FIG. 1 in an example use environment.

FIGS. 3-9 schematically depict the positioning apparatus 100 of FIGS. 1-2 in a sequence of use. Element labels are omitted for clarity from many individual structures of the positioning apparatus 100 in FIGS. 3-9. FIG. 3 depicts a native patient tissue, shown here as the upper portion of a femur including a femoral shaft 322 and a native femoral head 324. A locating pin 326 has been associated with the patient tissue, though such is not necessary for use of the positioning apparatus. Here, the locating pin 326 has been inserted into the femur 322 at a predetermined location on the femoral shaft, possibly with the help of preoperative or intraoperative imaging and/or a pin placement aid device (not shown). The locating pin 326 (or another locating pin, not shown) could also or instead be associated with the patient tissue through guidance by the positioning apparatus 100. Any of the described locating pins could be associated with the patient tissue in any desired manner and could remain in association with the patient tissue for any desired period of time and used to assist with any desired tasks, whether or not these tasks involve the positioning apparatus 100.

Figure 4:
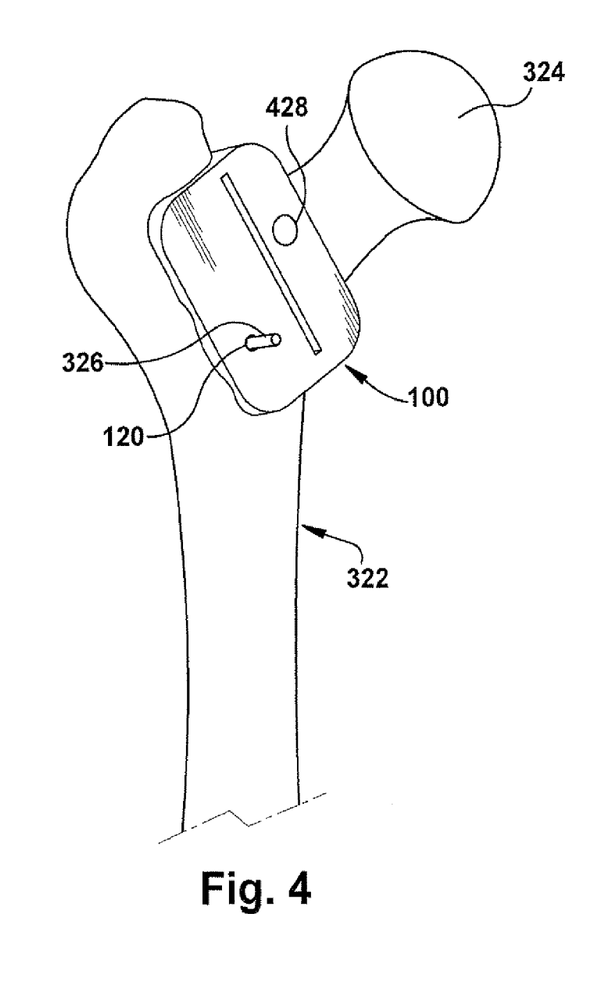

In FIG. 4, the locating pin aperture 120 has been engaged with the locating pin 326 by the locating pin aperture being placed over and slid down the locating pin. (As just stated, it is also contemplated that the locating pin 326 could be guided into association with the patient tissue by a previously placed positioning apparatus 100.) The engagement between the locating pin aperture 120 and the locating pin 326 may be as tight or loose as desired, even to a point of laxity at which the locating pin does not contact the inside of the locating pin aperture in the position shown in FIG. 4. In this Figure, additionally, the mating surface 204 has been mated with an outer surface of the femoral shaft 322 to provide at least one of securement, stability, and position indication for the locating block 102 relative to the femoral shaft.

As previously mentioned, the mating surface 204 had, prior to achieving the position shown in FIG. 4, been custom-configured for the femoral shaft 322 responsive to pre-operative imaging of the patient tissue to allow a single locating block 102 mating orientation relative to the femoral shaft. Stated differently, the contours of the mating surface 204 have been matched to the contours of the native patient tissue surface of the femoral shaft 322 to admit of only one nesting or mating orientation between the locating block 102 and the femoral shaft 322 when both are brought into mutual stable contact. This single-orientation mating characteristic between the locating block 102 and the femoral shaft 322 helps to assure the user that the cutting plane indicator 106 has been located stably in the desired location for the predetermined cutting procedure to take place. Any mismatch in orientation between the locating block 102 and the femoral shaft 322 will result in a wobbly, unstable contact to tactilely indicate to the user that the predetermined mating orientation has not been achieved.

In FIG. 4, the spacing arm 114 is not present and a spacing arm coupling feature 428 can be viewed. As depicted, the spacing arm coupling feature 428 is an aperture, which may extend partially into, or entirely through, the mass of the locating block 102, and is configured to selectively accept the first spacing arm end 116. The aperture providing the spacing arm coupling feature 428 may be shaped to permit the first spacing arm end 116 to be inserted in only one rotational orientation (i.e., to dictate the final position/orientation of the placement indicator 108). The spacing arm 114 may be separated from the locating block 102 at any phase of use of the positioning apparatus 100 and for any reason; for example, the spacing arm may be omitted during the resection phase if it otherwise might interfere with the desired cutting plane. In the latter case, the first spacing arm end 116 may be attached to the locating block 102 after the patient tissue has been resected through use of the cutting plane indicator 106. Alternately, however, the spacing arm 114 could be attached to the locating block 102 throughout the process of use of the positioning apparatus 100.

Figure 5:
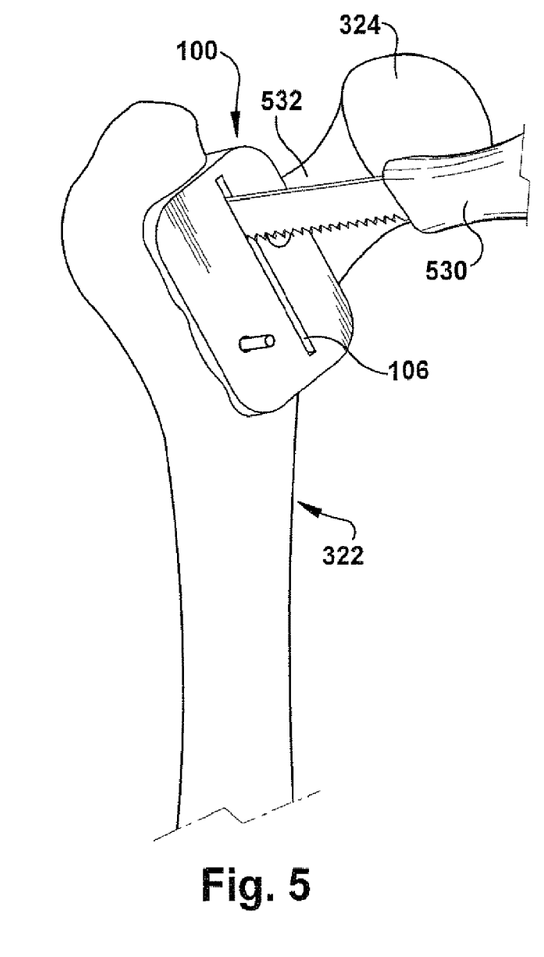

FIG. 5 illustrates the resection phase of use for the positioning apparatus 100. In this Figure, a cutting implement 530, such as the depicted bone saw, is guided by the cutting plane indicator 106 to resect the patient tissue along the desired cutting plane. Here, the desired cutting plane extends perpendicular to the plane of FIG. 5, is coincident with the cutting plane indicator 106, and severs the femoral head 324 from the femoral shaft 322 at the femoral neck 532. The cutting plane indicator 106 may be positioned on the locating block 102 as a result of preoperative planning to determine the desired cutting plane with respect to the patient tissue.

The user either contacts the cutting plane indicator 106 with the cutting implement 530, optionally in a sliding manner, or maintains the cutting implement in a desired non-contact relationship with the cutting plane during the resection process. The manner in which the guiding of the cutting implement 530 occurs may vary in different applications of the present invention, and may readily be provided by one of ordinary skill in the art with consideration of at least one of the type of cutting implement, nature and/or amount of the patient tissue to be removed, location and/or size of the surgical incisions, and any other suitable factors.

In the sequence of FIGS. 3-9, the entire femoral neck 532 is severed to completely release the femoral head 324. However, it is contemplated that the patient tissue may be partially severed or otherwise mechanically altered (cut, drilled, reamed, routed out, or the like), using one or more cutting implements 530 or other tools, as desired for a particular surgical procedure. Additional structures (not shown) could be temporarily or permanently provided to the positioning apparatus 100 to act as stops for partial cuts or otherwise to help guide the desired patient tissue alteration. These additional structures, when present, may be stock/standard items or may be custom-fitted to the patient in the bespoke manner of the mating surface 204.

Figure 6:
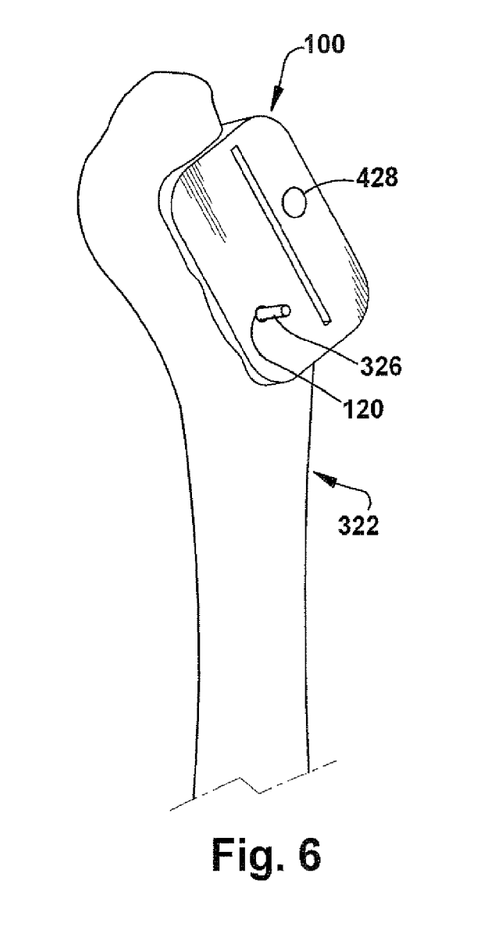

Turning to FIG. 6, the native femoral head 324 has been removed, leaving the resected patient tissue of the femoral shaft 322. (The actual resection cut line is concealed from view in this Figure by the locating block 102.) The cutting implement 530 has been removed from the surgical site, but the locating block 102 is maintained in the pre-established mating orientation/position with the femoral shaft 322 through continued nesting/mating contact between the mating surface 204 and the femoral shaft. The locating pin 326 is still engaged (whether loosely or tightly) with the locating pin aperture 120 in FIG. 6, as well, which may help to maintain the pre-established mating orientation/position.

While the femoral shaft 322 and locating block 102 are in the condition and orientation shown in FIG. 6, the user may perform additional, intermediate surgical processes. For example, the femoral shaft 322 could be reamed out to accept a stem of a prosthetic femoral implant component (not shown), the resected surface of the femoral shaft may be machined or altered, or any other desired surgical processes could be performed. Optionally, the locating block 102 could be temporarily removed from the femoral shaft 322 to facilitate a surgical process. When the locating block 102 is removed from the femoral shaft 322, the locating pin 326 may remain in place (e.g., as shown in FIG. 3) to help reorient the positioning apparatus into the FIG. 6 configuration when the surgical process prompting the removal has been completed. Alternately, the locating pin 326 may also be temporarily removed, leaving a hole in the femoral shaft 322 into which the locating pin can be reinserted as desired.

Figure 7:
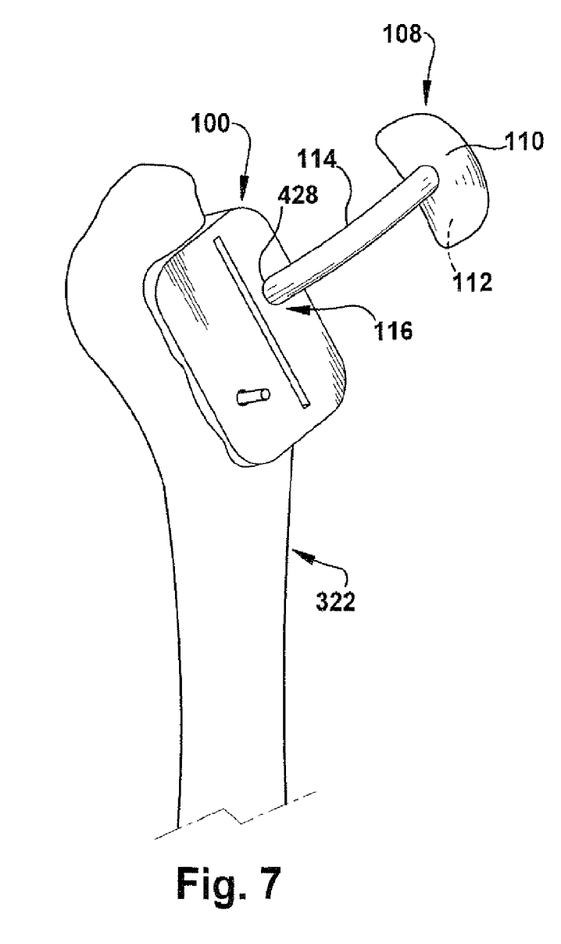

When all of the intermediate surgical processes have been performed and the locating block 102 has been re-mated with the femoral shaft 322 (if needed), the placement indicator 108 and spacing arm 114 can be attached to the locating block to form the configuration shown in FIG. 7. As shown, the first spacing arm end 116 has been inserted into the aperture in the locating block 102 which acts as the spacing arm coupling feature 428 in the schematically depicted arrangement. Any other suitable spacing arm coupling feature 428 and corresponding spacing arm 114 could be also or instead used to attach the spacing arm to the locating block 102. At the phase of use depicted in FIG. 7, the structures of the positioning apparatus 100 are functioning cooperatively to hold the component-contacting feature 110 (here, a concave surface functioning as a component-contacting surface 112) in a predetermined orientation with respect to the mating surface 204. Since the mating surface 204 is configured to nest in a predetermined mating relationship with the femoral shaft 322, the commutative property between the patient tissue (femoral shaft) and the positioning apparatus 100 results in the component-contacting surface 112 being located in a particular and predetermined orientation with the femoral shaft when the positioning apparatus is configured as shown in FIG. 7.

Figure 8:
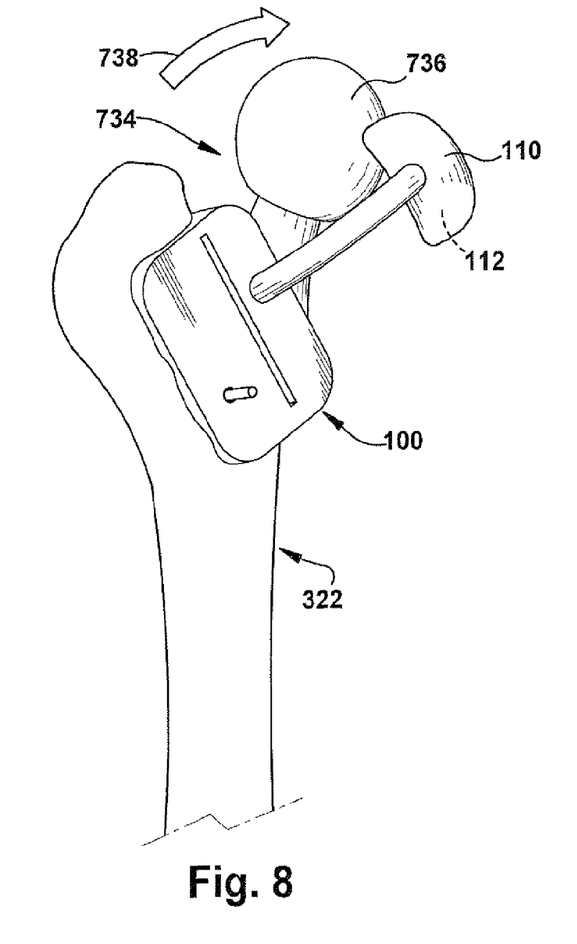

In FIG. 8, a prosthetic hip implant component 734, having a prosthetic femoral ball 736, has been placed in an initial implant position with respect to the femoral shaft 322. Here, a stem (not shown) of the prosthetic hip implant component 734 has been inserted into a prepared cavity (not shown) in the femoral shaft 322, as is commonly done in hip replacement surgeries. However, the prosthetic hip implant component 734, in the configuration of FIG. 7, is not in a desired final position, as evidenced between the separation between the prosthetic femoral ball 736 and the component-contacting feature 110. Therefore, the prosthetic hip implant component 734 needs to be adjusted with respect to the femoral shaft 322 to bring the prosthetic hip implant component toward a desired implant position.

This desired implant position may be, but is not necessarily, reflective of at least one of the original position of the native patient tissue being replaced by the prosthetic implant component and the existing position of a contralateral native patient tissue (e.g., the existing right hip femoral head when the left one is being replaced with a prosthetic version). The desired implant position can also or instead be determined pre-operatively by the user, optionally with the assistance of pre-operative scans of the native patient tissue and/or virtual models of the prosthetic implant component(s).

The adjustment needed in FIG. 8 to move the prosthetic hip implant component 734 to the desired implant position is a slight rotation (signified by clockwise arrow 738) within the femoral shaft 322. The engagement between the locating pin 326 and the locating pin aperture 120 may help to maintain the positioning apparatus 100 in the pre-established mating orientation/position during manipulation of the prosthetic hip implant component 734 and/or the femoral shaft 322.

Figure 9:
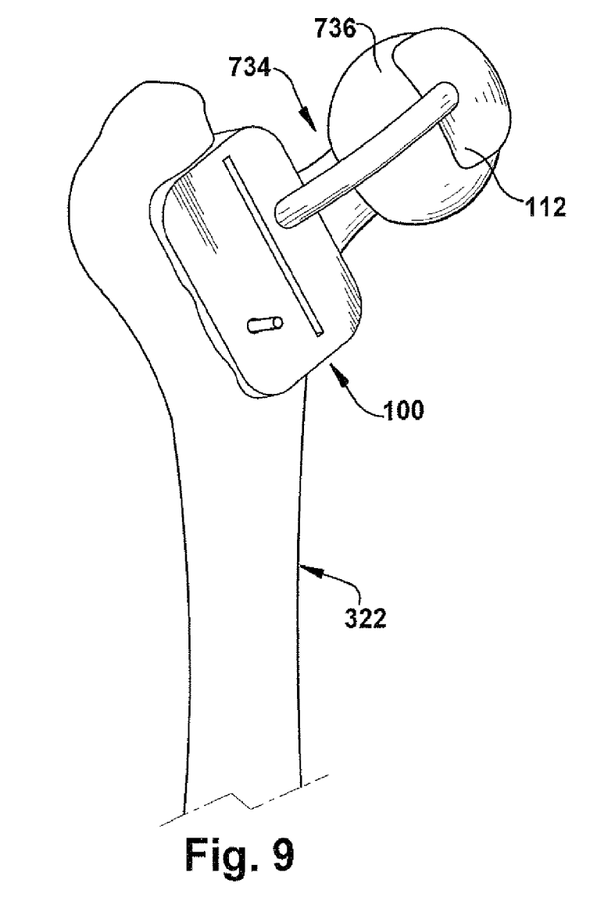

Once that clockwise rotation--or any other desired adjustment to bring an initially positioned implant toward a desired implant position—has been made, the prosthetic hip implant component 734 achieves the configuration shown in FIG. 9 with respect to the femoral shaft 322. As visible in FIG. 9, a preselected surface of the prosthetic hip implant component 734 (here, a portion of the convex surface of the prosthetic femoral ball 736) is brought into contact with at least a portion of the component-contacting feature 110 (here, the concave component-contacting surface 112) to indicate that the prosthetic hip implant component has achieved the desired implant position. Optionally, the component-contacting surface 112 may mate with the preselected surface of the prosthetic hip implant component 734 to indicate that the prosthetic hip implant component has achieved the desired implant position. Accordingly, the component-contacting surface 112 may have a contour selected to mirror the contour of the preselected surface of the prosthetic hip implant component 734.

The desired implant position may be based upon a spatial relationship with at least one of the native patient tissue and the positioning apparatus 100. For example, when the preselected surface of the prosthetic hip implant component 734 is located on a prosthetic femoral ball 736, the desired implant position may be a predetermined centering position with respect to at least one of the femoral shaft 322 and a native hip socket (not shown), and/or may be a predetermined height position with respect to the locating block 102.

It is contemplated that the component-contacting feature 110 need not be a component-contacting surface 112, but could instead be a tip of a finger- or rod-like structure (not shown) which contacts a preselected surface of the prosthetic implant component substantially at a single point on that preselected surface. It is also contemplated that the preselected surface of the prosthetic implant component could include a feature (not shown) configured to mate with the component-contacting feature 110, regardless of its form, for a positive location indication.

Figures 10, 11, 12:
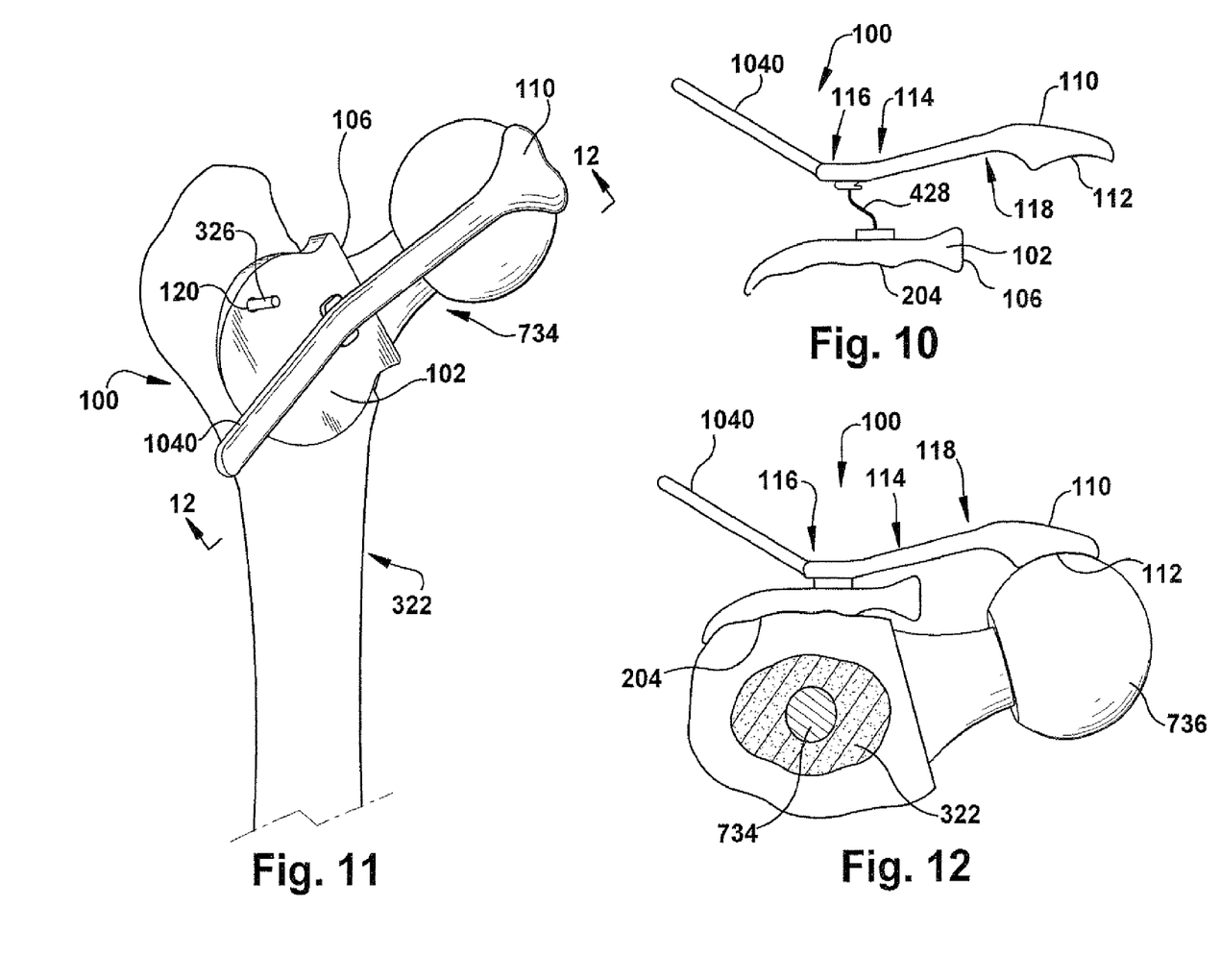
FIG. 10 is an exploded bottom view of an embodiment of the present invention.
FIG. 11 is a side view of the embodiment of FIG. 10 in the example use environment.
FIG. 12 is a cross-sectional view taken along line 12-12 of FIG. 11.

FIGS. 10-12 depict an example embodiment of the present invention. The embodiment shown in FIGS. 10-12 differs slightly from the schematic embodiment of FIGS. 1-9 in several ways. First, a handle 1040 is attached to the first spacing arm end 114, for selective attachment to the locating block 102. The handle 1040, when present, may assist with manipulation and/or steadying of the positioning apparatus 100 by a user. The cutting plane indicator 106 shown in FIGS. 10-12 is a cutting plateau, in contrast to the cutting slot shown in FIGS. 1-9. As can be seen in the exploded bottom view of FIG. 10, the spacing arm coupling feature 428 is a lug-and-bracket arrangement, in which a protrusion at the first spacing arm end 116 hooks onto an aperture of the locating block 102.

In the example use environment of FIGS. 11-12, shown as a hip replacement environment, the native femoral neck has already been severed to resect the native femoral head (not shown) and the prosthetic hip implant component 734 has been placed in the femoral shaft 322, as shown in the cross-sectional view of FIG. 12. Also in FIGS. 11-12, the prosthetic hip implant component 734 has been adjusted into the desired implant position, as evidenced by the mating relationship between the prosthetic femoral ball 736 and the component-contacting surface 112. (This mating relationship, and that between the mating surface 204 and the femoral shaft 322, are depicted with a slight gap therebetween for clarity of depiction here, but may be considered to be directly in contact in the use environment, as desired.)

Because the handle 1040, the spacing arm 114, and the component-contacting feature 110 are a unitary structure in the example use environment of FIGS. 10-12, the user may repeatedly associate and dissociate this unitary structure with the locating block 102 as desired during the surgical procedure. Engagement between the locating pin 326 and locating pin aperture 120 may assist in achieving and/or maintaining the mating relationship between the mating surface 204 and the femoral shaft 322, regardless of the position of this unitary structure with respect to the locating block 102.

The specific embodiment shown in FIGS. 10-12, or any other suitable embodiment of the present invention, may be used during a surgical procedure similarly to the use process described above with reference to the general, schematic embodiment of FIGS. 1-9.

A shoulder arthroplasty may include similar principles and surgical steps to those described above for a hip surgery. The device described can be adapted to the patient's surface anatomy of the proximal humerus. In a shoulder application, the cutting block may be placed over the anterior or superior surface anatomy of the humerus (depending upon the surgical exposure—i.e., the deltopectoral or superior approach, respectively). The location of the cutting block may be based upon the local bone anatomy defined by pre-operative imaging and the unique surface contour of the patient's native anatomy, and may be further defined by a spacing or extension arm attached from the cutting block to the apex and/or surface of the humeral head. These two features then help to locate the cutting block in the correct position to prescribe the humeral head osteotomy for the correct neck shaft angle and version as defined by the patient's anatomy and pre-operative imaging and surgical planning.

While aspects of the present invention have been particularly shown and described with reference to the preferred embodiment above, it will be understood by those of ordinary skill in the art that various additional embodiments may be contemplated without departing from the spirit and scope of the present invention. For example, the specific method described above for using the positioning apparatus 100 is merely illustrative; one of ordinary skill in the art could readily determine any number of tools, sequences of steps, or other means/options for placing the apparatus, or components thereof, into positions substantively similar to those shown and described herein. Though the cutting plane indicator 106 is shown as being simply linear and described as a physical indication of a desired cutting plane, the guided cutting motion could also or instead encompass a curvilinear, curved, multi-angle linear, or otherwise not-simply-linear cutting plane indicator (not shown), being a physical indication of a possibly non-planar desired cutting contour. Any of the described structures and components could be integrally formed as a single piece or separately provided of any suitable material or combinations of materials; however, the chosen material(s) should be biocompatible for most applications of the present invention. The mating relationships formed between the described structures need not keep the entirety of each of the "mating" surfaces in direct contact with each other but could include spacers or holdaways for partial direct contact, a liner for indirect contact, or could even be approximated with intervening space remaining therebetween and no contact. Though certain components described herein are shown as having specific geometric shapes, all structures of the present invention may have any suitable shapes, sizes, configurations, relative relationships, cross-sectional areas, or any other physical characteristics as desirable for a particular application of the present invention. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

The invention claimed is:

1. A method of guiding resection of a patient tissue and guiding placement of a prosthetic implant component in a desired implant position with respect to the resected patient tissue, the method comprising the steps of:
placing a mating surface of a locating block in mating contact with the patient tissue, the mating surface being custom-configured for the patient tissue responsive to pre-operative imaging of the patient tissue to allow a single locating block mating orientation relative to the patient tissue;
providing a physical indication of a desired cutting plane for the resection using a cutting plane indicator included on the locating block; providing a placement indicator, spaced apart from the locating block and including a component-contacting feature;
spacing the placement indicator apart from the locating block with an elongate spacing arm, the spacing arm having oppositely disposed first and second spacing arm ends, the first spacing arm end being attached to the locating block and the second spacing arm end being attached to the placement indicator;
placing the component-contacting feature of the placement indicator at a predetermined placement position in three-dimensional space relative to the patient tissue with the spacing arm, the placement position predetermination being at least partially based upon pre-operative imaging of the patient tissue;
guiding a cutting implement with the cutting plane indicator to resect the patient tissue along the desired cutting plane when the mating surface is in mating contact with the patient tissue; placing the prosthetic implant component in an initial implant position with respect to the patient tissue;
adjusting the prosthetic implant component with respect to the patient tissue to bring the prosthetic implant component toward a desired implant position; and
bringing a preselected surface of the prosthetic implant component into contact with the component-contacting feature to indicate that the prosthetic implant component has achieved the desired implant position.

2. The method of claim 1, wherein the step of guiding a cutting implement with the cutting plane indicator includes the step of moving the cutting implement in guiding contact with the cutting plane indicator during resection of the patient tissue.

3. The method of claim 1, including the steps of: associating a locating in with the patient tissue; engaging a locating pin aperture of the locating block with the locating pin; and providing the locating block with at least one of securement, stability, and position indication relative to the patient tissue through the engagement of the locating pin aperture with the locating pin.

4. The method of claim 1, wherein the spacing arm is separately provided from the locating block, the locating block includes a spacing arm coupling feature for selectively receiving the first spacing arm end, and including the step of attaching the first spacing arm end to the locating block after the step of guiding a cutting implement with the cutting plane indicator to resect the patient tissue has been performed.

5. The method of claim 1, wherein the component-contacting feature is a component-contacting surface shaped to mate with the preselected surface of the prosthetic implant component, and wherein the step of bringing a preselected surface of the prosthetic implant component into contact with the component-contacting feature includes the step of mating the component-contacting surface with the preselected surface of the prosthetic implant component to indicate that the prosthetic implant component has achieved the desired implant position.

6. A method of guiding resection of a patient tissue and guiding placement of a prosthetic implant component in a desired implant position with respect to the resected patient tissue, the method comprising the steps of:
placing a mating surface of a locating block in mating contact with the patient tissue, the mating surface being custom-configured for the patient tissue responsive to pre-operative imaging of the patient tissue to allow a single locating block mating orientation relative to the patient tissue, and using a cutting plane indicator of the locating block to provide a physical indication of a desired cutting plane for the resection;
using an elongate spacing arm to space apart a placement indicator having a component-contacting feature from the locating block, including placing the component-contacting feature of the placement indicator at a predetermined placement position in three-dimensional space relative to the patient tissue with the spacing arm, the placement position predetermination being at least partially based upon pre-operative imaging of the patient tissue;
guiding a cutting implement with the cutting plane indicator to resect the patient tissue along the desired cutting plane when the mating surface is in mating contact with the patient tissue;
placing the prosthetic implant component in an initial implant position with respect to the patient tissue, and adjusting the prosthetic implant component with respect to the patient tissue to bring the prosthetic implant component toward a desired implant position; and
bringing a preselected surface of the prosthetic implant component into contact with the component-contacting feature of the placement indicator to indicate that the prosthetic implant component has achieved the desired implant position.

7. The method of claim 6, wherein the step of guiding a cutting implement with the cutting plane indicator includes the step of moving the cutting implement in guiding contact with the cutting plane indicator during resection of the patient tissue.

8. The method of claim 6, further comprising the steps of: associating a locating pin with the patient tissue; engaging a locating pin aperture of the locating block with the locating pin; and providing the locating block with at least one of securement, stability, and position indication relative to the patient tissue through the engagement of the locating pin aperture with the locating pin.

9. The method of claim 6, wherein the spacing arm is separately provided from the locating block and includes oppositely disposed first and second spacing arm ends, the first spacing arm end being attached to the locating block and the second spacing arm end being attached to the placement indicator, the locating block includes a spacing arm coupling feature for selectively receiving the first spacing arm end, and including the step of attaching the first spacing arm end to the locating block after the step of guiding a cutting implement with the cutting plane indicator to resect the patient tissue has been performed.

10. The method of claim 6, wherein the component-contacting feature is a component-contacting surface shaped to mate with the preselected surface of the prosthetic implant component, and wherein the step of bringing a preselected surface of the prosthetic implant component into contact with the component-contacting feature includes the step of mating the component-contacting surface with the preselected surface of the prosthetic implant component to indicate that the prosthetic implant component has achieved the desired implant position.

\* \* \* \* \*